United States Patent [19]

Denzel et al.

[11] 4,075,210
[45] Feb. 21, 1978

[54] PYRAZOLO[1,5-a]PYRIDO[4,3-d]PYRIMIDIN-9(4H)-ONE AND DERIVATIVES THEREOF

[75] Inventors: Theodor Denzel, Regensberg; Hans Hoehn, Tegernheim, both of Germany

[73] Assignee: E. R. Squibb & Sons, Inc., Princeton, N.J.

[21] Appl. No.: 783,252

[22] Filed: Mar. 31, 1977

[51] Int. Cl.$^2$ .................. A61K 31/415; C07D 471/04
[52] U.S. Cl. ...................... 260/256.4 F; 260/256.5 R; 260/295.5 R; 424/251
[58] Field of Search ................... 260/256.5 R, 256.4 F

[56] References Cited

U.S. PATENT DOCUMENTS

| 3,150,136 | 9/1964 | Wolfrum et al. | 260/256.4 F |
| 3,171,740 | 3/1965 | Menzel et al. | 260/256.4 F |
| 3,787,408 | 1/1974 | Takamizawa et al. | 260/256.4 F |

Primary Examiner—Donald G. Daus
Assistant Examiner—James H. Turnipseed
Attorney, Agent, or Firm—Lawrence S. Levinson; Merle J. Smith

[57] ABSTRACT

Pyrazolo[1,5-a]pyrido[4,3-d]pyrimidin-9(4H)-one and derivatives thereof have the general formula

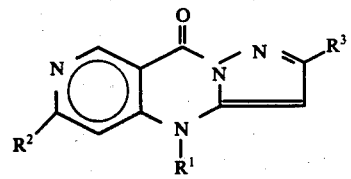

The compounds are useful as antiinflammatory agents.

16 Claims, No Drawings

PYRAZOLO[1,5-a]PYRIDO[4,3-d]PYRIMIDIN-9(4H)-ONE AND DERIVATIVES THEREOF

SUMMARY OF THE INVENTION

This invention relates to the new compound pyrazolo[1,5-a]pyrido[4,3-d]pyrimidin-9(4H)-one and new derivatives thereof. These new compounds have the general formula (I)

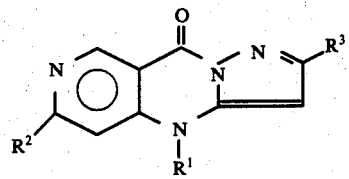

$R^1$ is hydrogen or lower alkyl.
$R^2$ is hydrogen, halogen, lower alkylthio, lower alkoxy or lower alkylamino.
$R^3$ is hydrogen or lower alkyl.

DETAILED DESCRIPTION OF THE INVENTION

The substituents represented by the symbols have the following meanings throughout this specification.

The lower alkyl groups are straight or branched chain aliphatic hydrocarbon groups having up to seven carbon atoms like methyl, ethyl, propyl, isopropyl, butyl, sec.-butyl, t-butyl, amyl, isoamyl and the like. The $C_1$-$C_4$ members, especially the $C_1$-$C_2$ members and most especially the $C_1$ member, are preferred.

The lower alkylthio, lower alkoxy and lower alkylamino groups have alkyl groups of the type described above attached to a sulfur, oxygen or nitrogen atom, respectively. These include, for example, methylthio, ethylthio, propylthio, butylthio or the like, methoxy, ethoxy, propoxy, isopropoxy, butoxy or the like, methylamino, ethylamino, propylamino, butylamino, t-butylamino or the like.

The halogens include the four common halogens, preferably chlorine and bromine, especially chlorine.

The new compounds of formula I are formed by the following series of reactions.

A 4,6-dihalopyridinecarboxylic acid ester [produced according to the procedure of G. Lhommet and P. Maitte, C.R. Acad. Sci., Ser. C 275, 1317 (1972)] of the formula

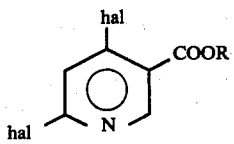

(wherein R is lower alkyl and hal is halogen, preferably chloro) is made to react with an appropriate aminopyrazole of the formula

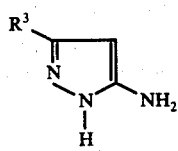

The reaction is effected in a solvent like butyl alcohol, dimethylformamide, acetic acid, or the like. By this reaction a compound of the formula

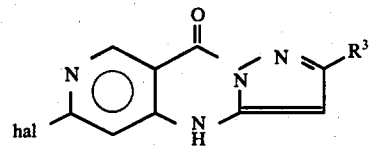

is produced.

Compounds of the formula

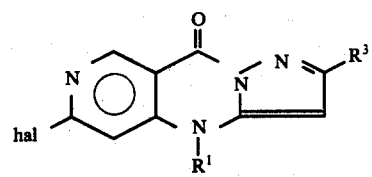

wherein $R^1$ is other than hydrogen are now produced by the reaction of the compound of formula Ia with an alkyl halide in the presence of an inorganic base like potassium carbonate in a solvent like dimethylformamide.

Compounds of the formula

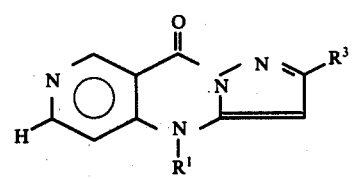

wherein $R^2$ is hydrogen can be produced by catalytic hydrogenation of a compound of formula Ia or Ib in the presence of palladium on charcoal as catalyst and a base like triethylamine.

Compounds of the formula

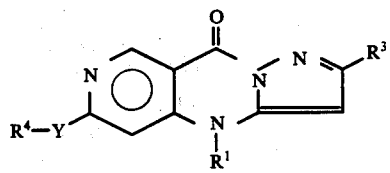

wherein $R^2$ is lower alkylthio or lower alkoxy, represented in formula Id by $R^4$, $R^4$ being lower alkyl and Y being sulfur or oxygen, are prepared by reacting a compound of formula Ia or Ib with the appropriate alkali metal alkoxide or alkali metal mercaptide in an organic solvent like alcohol or dimethylformamide.

Compounds of the formula

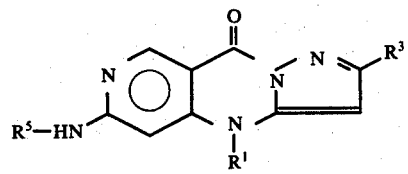

wherein $R^2$ is alkylamino, i.e., $R^5$ in formula Ie is lower alkyl, are prepared by reaction of a compound of formula Ia or Ib with the corresponding lower alkylamine.

The new compounds of this invention have antiinflammatory properties and are useful as antiinflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carrageenan edema assay or delayed hypersensitivity reaction assay in rats. The active substance can be utilized in compositions such as tablets, capsules, solutions or suspensions containing up to about 300 mg. per unit of dosage of a compound or mixture of compounds of formula I. they may be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion or cream may be used.

The following examples are illustrative of the invention and constitute especially preferred embodiments. They also serve as models for the preparation of other members of the group which can be produced by suitable substitution of starting materials. Temperatures are in degrees Celsius.

EXAMPLE 1

6-Chloropyrazolo[1,5-a]pyrido[4,3-d]pyrimidin-9(4H)-one 205 g. of 4,6-dichloropyridine-3-carboxylic acid, methyl ester and 166 g. of 5-aminopyrazole are refluxed together in 300 ml. of acetic acid for 10 hours with stirring. The crystalline 6-chloropyrazolo[1,5-a]pyrido[4,3-d]pyrimidin-9(4H)-one is filtered off, washed with water and recrystallized from dimethylformamide, yield: 185 g. (84%); m.p. > 300°.

EXAMPLE 2

Pyrazolo[1,5-a]pyrido[4,3-d]pyrimidin-9(4H)-one 22 g. of 6-chloropyrazolo[1,5-a]pyrido[4,3-d]pyrimidin-9(4H)-one of Example 1 are hydrogenated in 200 ml. of dimethylformamide in the presence of 15 g. of triethylamine and 10% palladium on charcoal as catalyst at 80° and 3 atmospheres hydrogen pressure. When the theoretical amount of hydrogen has been absorbed, the reaction is stopped and the mixture is filtered after cooling to room temperature. After evaporation of the solvent, the crystalline residue, pyrazolo[1,5-a]pyrido[4,3-d]pyrimidin-9(4H)-one, is recrystallized from dimethylformamide, yield: 13 g. (70%); m.p. >300°.

EXAMPLE 3

6-Chloro-2-methylpyrazolo[1,5-a]pyrido[4,3-d]pyrimidin-9(4H)-one 205 g. of 4,6-dichloropyridine-3-carboxylic acid, methyl ester and 194 g. of 5-amino-3-methylpyrazole are refluxed together in 500 ml. of butyl alcohol with stirring for 24 hours. After this time, 6-chloro-2-methylpyrazolo[1,5-a]pyrido[4,3-d]pyrimidin-9(4H)-one is filtered off, washed with water and recrystallized from dimethylformamide, yield: 195 g. (83%); m.p. >300°.

EXAMPLE 4

2-Methylpyrazolo[1,5-a]pyrido[4,3-d]pyrimidin-9(4H)-one 23.5 g. of 6-chloro-2-methylpyrazolo[1,5-a]pyrido[4,3-d]pyrimidin-9(4H)-one of Example 3 are hydrogenated at 80° in 200 ml. of dimethylformamide in the presence of 15 g. of triethylamine and 10% palladium on charcoal as catalyst. When the theoretical amount of hydrogen has been absorbed, the reaction mixture is filtered hot and the mother liquor evaporated in vacuo to dryness. The remaining 2-methylpyrazolo[1,5-a]pyrido[4,3-d]pyrimidin-9(4H)-one is recrystallized from dimethylformamide, yield: 18.5 g. (92%); m.p. >300°.

EXAMPLE 5

6-Chloro-2,4-dimethylpyrazolo[1,5-a]pyrido[4,3-d]pyrimidin-9(4H)-one 23.5 g. of 6-chloro-2-methylpyrazolo[1,5-a]pyrido[4,3-d]pyrimidin-9(4H)-one of Example 3 are suspended in 200 ml. of dimethylformamide. 20 g. of potassium carbonate and 16 g. of methyl iodide are added. The mixture is stirred at 80° for 24 hours. After this time, the mixture is cooled and the precipitate filtered off. The crystalline product, 6-chloro-2,4-dimethylpyrazolo[1,5-a]pyrido[4,3-d]pyrimidin-9(4H)-one is washed several times with water and then recrystallized from dimethylformamide, yield: 18 g. (72%); m.p. >300°.

EXAMPLE 6

6-Chloro-4-methylpyrazolo[1,5-a]pyrido[4,3-d]pyrimidin-9(4H)-one

By treating 6-chloropyrazolo[1,5-a]pyrido[4,3-d]pyrimidin-9(4H)-one of Example 1 with methyl iodide according to the procedure of Example 5 for the preparation of 6-chloro-2,4-dimethylpyrazolo[1,5-a]pyrido[4,3-d]pyrimidin-9(4H)-one, 6-chloro-4-methylpyrazolo[1,5-a]pyrido[4,3-d]pyrimidin-9(4H)-one is obtained, yield: 76%; m.p. >300°.

EXAMPLE 7

4-Methylpyrazolo[1,5-a]pyrido[4,3-d]pyrimidin-9(4H)-one

By hydrogenating 6-chloro-4-methylpyrazolo[1,5-a]pyrido[4,3-d]pyrimidin-9(4H)-one of Example 6 by the procedure described in Example 4 for 6-chloro-2-methylpyrazolo[1,5-a]pyrido[4,3-d]pyrimidin-9(4H)-one, 4-methylpyrazolo[1,5-a]pyrido[4,3-d]pyrimidin-9(4H)-one is obtained, yield: 83%; m.p. >300°.

EXAMPLE 8

2,4-Dimethylpyrazolo[1,5-a]pyrido[4,3-d]pyrimidin-9(4H)-one

By substituting for the 6-chloro-2-methylpyrazolo[1,5-a]pyrido[4,3-d]pyrimidin-9(4H)-one in the procedure of Example 4, 6-chloro-2,4-dimethylpyrazolo[1,5-a]pyrido[4,3-d]pyrimidin-9(4H)-one, 2,4-dimethylpyrazolo[1,5-a]pyrido[4,3-d]pyrimidin-9(4H)-one is formed, yield: 76%; m.p. >300° (DMF).

EXAMPLE 9

2,4-Dimethyl-6-(methylthio)pyrazolo[1,5-a]pyrido[4,3-d]pyrimidin-9(4H)-one 0.1 mole of 6-chloro-2,4-dimethylpyrazolo[1,5-a]pyrido[4,3-d]pyrimidin-9(4H)-one of Example 5 is suspended in 100 ml. of dimethylformamide. 0.15 mole of sodium methyl mercaptide is added and the mixture is heated at reflux temperature with stirring for 10 hours. After this time, the precipitated sodium chloride is filtered off and 100 ml. of water are added. 2,4-dimethyl-6-(methylthio)pyrazolo[1,5-a]pyrido[4,3-d]pyrimidin-9(4H)-one crystallizes and is filtered off, yield: 73%; m.p. >300° (butyl alcohol).

EXAMPLE 10

4-Methyl-6-(methylthio)pyrazolo[1,5-a]pyrido[4,3-d]pyrimidin-9(4H)-one

When 6-chloro-2,4-dimethylpyrazolo[1,5-a]pyrido[4,3-d]pyrimidin-9(4H)-one of Example 9 is replaced by 6-chloro-4-methylpyrazolo[1,5-a]pyrido[4,3-d]pyrimidin-9(4H)-one of Example 6, 4-methyl-6-(methylthio)pyrazolo[1,5-a]pyrido[4,3-d]pyrimidin-9(4H)-one is obtained, yield: 68%; m.p. 267.4° (butyl alcohol).

Example 11

4-Methyl-6-methoxypyroazolo[1,5-a]pyrido[4,3-d]pyrido[4,3-d]pyrimidin-9(4H)-one 0.01 mole of 6-chloro-4-methylpyrazolo[1,5-a]pyrido[4,3-d]pyrimidin-9(4H)-one are added to a solution of 0.015 mole of sodium in 50 ml. of dry methanol. The solution is refluxed for 24 hours. After this time, the solvent is distilled off and the residue treated with 10 ml. of water and then filtered off. The product, 4-methyl-6-methoxypyrazolo[1,5-a]pyrido[4,3-d]pyrimidin-9(4H)-one, is recrystallized from butanol, yield: 83%; m.p. 287.3°.

EXAMPLE 12

4-Methyl-6-methylaminopyrazolo[1,5-a]pyrido[4,3-d]pyrimidin-9(4H)-one 0.01 mole of 6-chloro-4-methylpyrazolo[1,5-a]pyrido[4,3-d]pyrimidin-9(4H)-one is treated in 50 ml. of dimethylformamide with 10 ml. of methylamine in an autoclave at 100° for 10 hours. The solvent is distilled off, the residue treated with 10 ml. of water and the crystalline 4-methyl-6-methylaminopyrazolo[1,5-a]pyrido[4,3-d]pyrimidin-9(4H)-one is filtered off, yield: 74%; m.p. >300° (DMF).

What is claimed is:

1. A compound of the formula

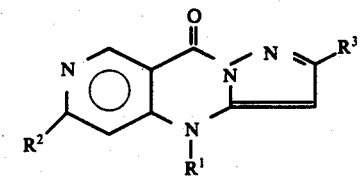

wherein
$R^1$ and $R^3$ each is hydrogen or lower alkyl; and
$R^2$ is hydrogen, halogen, lower alkylthio, lower alkoxy or lower alkylamino.

2. A compound as in claim 1 wherein $R^2$ is halogen.
3. A compound as in claim 2 wherein the halogen is chlorine.
4. A compound as in claim 1 wherein the lower alkyl groups are methyl.
5. A compound as in claim 1 wherein $R^2$ is hydrogen.
6. A compound as in claim 1 wherein $R^2$ is lower alkylthio.
7. A compound as in claim 1 wherein $R^2$ is lower alkoxy.
8. A compound as in claim 1 wherein $R^2$ is lower alkylamino.
9. A compound as in claim 1 wherein $R^1$, $R^2$ and $R^3$ each is hydrogen.
10. A compound as in claim 1 wherein $R^1$ and $R^2$ each is hydrogen and $R^3$ is methyl.
11. A compound as in claim 1 wherein $R^1$ and $R^3$ each is methyl and $R^2$ is methylthio.
12. A compound as in claim 1 wherein $R^1$ is methyl, $R^2$ is methylthio and $R^3$ is hydrogen.
13. A compound as in claim 1 wherein $R^1$ is methyl, $R^2$ is methoxy and $R^3$ is hydrogen.
14. A compound as in claim 1 wherein $R^1$ is methyl, $R^2$ is methylamino and $R^3$ is hydrogen.
15. A compound as in claim 1 wherein $R^1$ is methyl and $R^2$ and $R^3$ each is hydrogen.
16. A compound as in claim 1 wherein $R^1$ and $R^3$ each is methyl and $R^2$ is hydrogen.